United States Patent [19]

Mathew et al.

[11] Patent Number: 4,614,813
[45] Date of Patent: Sep. 30, 1986

[54] PROCESS FOR THE PREPARATION OF N-HYDROXY ORGANO IMIDATE COMPOUNDS

[75] Inventors: Chempolil T. Mathew, Randolph; Harry E. Ulmer, Morristown, both of N.J.

[73] Assignee: Allied Corporation, Morris Township, Morris County, N.J.

[21] Appl. No.: 599,433

[22] Filed: Apr. 12, 1984

[51] Int. Cl.$^4$ ............................................ C07C 119/18
[52] U.S. Cl. ........................................................ 558/7
[58] Field of Search ...................... 260/453.8; 558/7, 3

[56] References Cited

U.S. PATENT DOCUMENTS 4,029,688  6/1977  D'Silva ............................ 260/453.8

OTHER PUBLICATIONS

Smith, The Chemistry of Open-Chain Organic Nitrogen Compounds, vol. II, p. 59, Benjamic Pub. (1966).
The Merck Index, ninth edition, p. ONR-94, Merck and Co. pub. (1976).

*Primary Examiner*—Henry R. Jiles
*Assistant Examiner*—Robert C. Whittenbaugh
*Attorney, Agent, or Firm*—Richard C. Stewart, II; Gerhard H. Fuchs; Alan M. Doernberg

[57] ABSTRACT

This invention relates to a process for preparing N-hydroxyl organo imidate compounds by reacting an oxime compound with a halogenating agent and reacting the resulting 1-halosubstituted oxime compound with the alkali metal or alkaline earth metal salt of an alcohol.

24 Claims, No Drawings

PROCESS FOR THE PREPARATION OF N-HYDROXY ORGANO IMIDATE COMPOUNDS

BACKGROUND OF THE INVENTION

1. Field of the Invention

This invention relates to a novel process for preparing N-hydroxy organo imidate compounds. More particularly, this invention is directed to a process for preparing N-hydroxy organo imidate compounds by halogenating the corresponding oxime compound in an organic solvent which does not react with the halogenation agent under the reaction condition, and reacting the resulting 1-halo substituted oxime compound with the alkali metal or alkaline earth metal salt of an alcohol.

2. Prior Art

The classical method of preparing N-hydroxy organo imidate compounds involves reacting the corresponding iminoester hydrochloride compound and hydroxylamine hydrochloride. For example, J. Houben and E. Schmidt, Chem. Ber. 46, 3616 (1913), and Y. Tamura et al., J. Org. Chem. 38, 6 1239 (1973) describe the preparation of ethyl N-hydroxyacetimidate by reacting acetiminoethylester hydrochloride and hydroxylamine hydrochloride in accordance with the following reaction scheme:

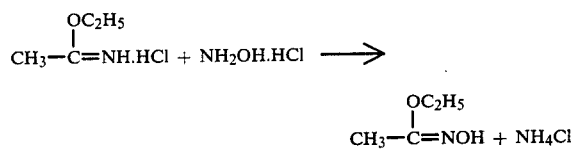

The reported yield was 66.3%.

A. Werner and H. Buss, Chem Ber. 27, 2193 (1894) has reported an attempted reaction of α-chlorobenzaldehyde oxime with sodium ethoxide, in which ethyl N-hydroxy benzimidate was identified along with diphenyl urea as reaction products.

SUMMARY OF THE INVENTION

According to the present invention there is provided a process for preparing a compound of the formula:

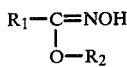

wherein:

$R_1$ is substituted or unsubstituted alkyl, alkoxyalkyl, cycloalkyl or phenylalkyl wherein permissible substituents are one or more halogen, nitro, cyano and perhaloalkyl groups; and $R_2$ is alkyl, alkenyl, alkynyl, alkoxyalkyl, cycloalkyl, cycloalkenyl, phenyl, or phenylalkyl, either unsubstituted or substituted with one or more cyano, nitro, halogen, alkyl, alkoxy, perhaloalkyl, alkylthio, arylthio, alkylsulfinyl, alkoxycarbonyl, alkylsulfonyl or amido groups, which process comprises the steps of;

(a) reacting an organo oxime compound of the formula $R_1CH=NOH$ with a halogenating agent in an organic solvent which is substantially non-reactive with said halogenating agent to form the corresponding 1-halo oxime compound; and (b) reacting said 1-halo oxime compound in said solvent with an alkaline earth metal or alkali metal alcoholate of the formula $R_2OM$ wherein M is an alkali metal or alkaline earth metal cation.

DESCRIPTION OF THE PREFERRED EMBODIMENTS

The process of this invention consist of two essential steps. A preferred embodiment of the first essential step of the process of this invention is described schematically in the following Reaction Step A:

Reaction Step A

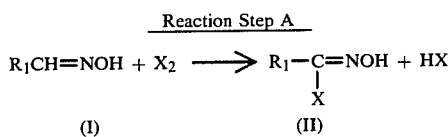

wherein $R_1$ is as defined hereinabove, and $X_2$ is halogen. The halogenation step to form the 1-halo oxime compound is conveniently performed by reacting a halogenating agent and an oxime compound of the formula $R_1CH=NOH$ in an organic solvent which is substantially non-reactive with the halogenation agent. Through use of the organic solvent the formation of by-products is minimized, product yields are increased and the resulting products can be purified without resorting to elaborate and costly purification techniques.

Useful organic solvents include those solvents which do not include any functional groups which are reactive with the halogenation agent. For example, when elemenatal halogen is used as the halogenation agent permissible functional groups are those which are not oxidizable by the halogen and which are not displaceable by halogen, or which are not susceptible to addition by the halogen under the reaction conditions of the process. Illustrative of such solvents are non-reactive alcohols such as methanol, and the like; and halohydrocarbons such as carbon tetrachloride, methylene dichloride, chloroform, chlorotrifluoro methane, dichlorodifluoro ethane, trichlorotrifluoro ethane, and the like. While the halogenation step of the reaction is preferably conducted in a non-reactive solvent, in instances where the oxime compound is liquid an excess of the oxime reactant can be employed as the reaction solvent. Preferred organic solvents for use in the practice of this invention are methanol and halohydrocarbons, and particularly preferred for use in the process are methanol, chloroform and carbon tetrachloride.

Oxime compounds which are useful as reactants in the conduct of the process of this invention are of the formula:

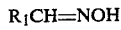

in which $R_1$ is as described above. Such compounds are well known to those of skill in the art and include aldoxime compounds wherein $R_1$ is alkyl, such as acetaldehyde oxime, propionaldehyde oxime, n-butyraldehyde oxime, isobutyraldehyde oxime, n-valeraldehyde oxime, pivalaldehyde oxime and the like. Illustrative of suitable oxime reactants in which $R_1$ is cycloalkyl are cyclohexanecarboxaldehyde oxime, cyclopentanecarboxaldehyde oxime, 2,2-dimethylcyclohexanecarboxaldehyde oxime, cycloheptanecarboxaldehyde oxime and the like. Suitable oxime compounds in which $R_1$ is alkoxyalkyl include 2-methoxyacetaldehyde oxime, 2-ethoxypropionaldehyde oxime, 3-butoxybutyraldehyde oxime, 2-propoxyvaleraldehyde oxime and the like. Exemplary of useful oxime reactants in which $R_1$ is phenylalkyl are 2-phenylpropionaldehyde oxime, 3-phenylvaleraldehyde oxime, 2-benzylpropionaldehyde oxime, phenylacetaldehyde oxime, 2-ethyl-2-phenyl acetaldehyde oxime, and the like. As was noted above, $R_1$ substituents may be substituted with one or more functional groups which are relatively non-reactive with the halogenating agent employed in the process under the process conditions. Illustrative of such non-reactive functional groups in embodiments of the invention in which elemental halogen is the halogenating agent of choice are halogen, i.e. fluorine, chlorine, bromine or iodine, alkoxy i.e., methoxy, ethoxy, propoxy and the like, as well as nitro, cyano, carboxy, alkoxycarbonyl, perfluoroalkyl, i.e., trifluoromethyl, and like non-reactive functional groups.

Preferred for use in the practice of this invention are oxime compounds of the above formula in which $R_1$ is alkyl having from 1 to about 7 carbon atoms and phenylalkyl having from 7 to about 14 carbon atoms and particularly preferred for use are aldoximes in which $R_1$ is alkyl having from 1 to about 4 carbon atoms, and phenylalkyl having from 7 to about 11 carbon atoms. Amongst these particularly preferred embodiments most preferred are those embodiments in which $R_1$ is alkyl having from 1 to about 4 carbon atoms with compounds in which $R_1$ is methyl, ethyl, propyl or isopropyl being especially preferred.

The quantity of aldoxime employed is not critical and can vary widely. Usually, the quantity of aldoxime will vary from about 5 to about 75 percent by weight based on the total weight of the solvent. The preferred amount of the aldoxime reactant is from about 10 to about 25 weight percent. Greater amounts of solvent can of course be used, except such amounts merely dilute the components in the reaction mass with no particular advantage being obtained.

The oxime compounds utilized as reactants in the process of this invention can be conveniently prepared according to conventional methods. For example, these compounds can be conveniently prepared by reacting an appropriate aldehyde with hydroxylamine salts in the presence of a base, such as ammonia, an alkali metal hydroxide or carbonate. Another method involves reacting the corresponding aldehyde in a water medium with sodium nitrite, sodium bisulfite and sulfur dioxide.

The halogenation agent employed is not critical and can be varied widely. Useful halogenation agents include elemental halogen. Chlorine is the preferred halogenating agent for economic reasons, however, other chlorination agents, such as sulfuryl chloride, and the like, can be used if desired.

In general, the oxime reactant will be treated with a stoichiometric quantity of the halogen or other halogenating agent. An excess or less than stoichiometric amounts of the halogenating agent may also be employed. In the preferred embodiments of this invention the quantity of halogen may vary from the stoichiometric amount by from plus or minus one percent. In general, when a halogen is the halogenation agent of choice halogenating can be effected by adding the solid, liquid or gaseous halogen into a solution of the oxime compound in an appropriate solvent, or in the liquid oxime compound. In general, the halogen is reacted with at least a stoichiometric quantity of the oxime compound, however, as much as a 50 percent excess or more of the oxime can be used. In the preferred embodiments of the invention, the quantity of oxime employed may vary from a stoichiometric amount to plus or minus 10 percent, and in the particularly preferred embodiments will vary from a stoichiometric amount to plus or minus 5 percent.

The reaction temperature of the halogenation step can vary from the freezing point of the reaction mixture up to the temperature at which the 1-halo substituted oxime reaction product becomes susceptible to violent decomposition. In the case of chloroacetaldehyde oxime, this upper reaction temperature is about 25° C. In the preferred embodiments of the invention, reaction temperatures will vary from about $-10°$ C. to about $+10°$ C., and in the particularly preferred embodiments of this invention the reaction temperatures will vary from about $-5°$ C. to about $+5°$ C. Amongst these particularly preferred embodiments most preferred are those embodiments in which the reaction temperature varies from about $-2°$ C. to about $+2°$ C.

Halogenation addition rates are also not critical and can vary widely depending on the ability to control or maintain the reaction medium temperature within the prescribed range, and on factors known to those of skill. Usually, when a halogen is the halogenation agent of choice, the halogen can be added quite rapidly. For example, halogen addition times of from about 10 minutes to several hours can be employed. In the preferred embodiments of the invention the halogen addition is completed in less than an hour.

After completion of the halogenation reaction, the reaction mixture can be reacted in situ with an appropriate Alkali metal or Alkaline earth metal alcoholate in the second essential step of the process of this invention, or can be isolated from the reaction mixture for use in the second step of the process at some later time. The second essential step of the process of this invention is described schematically in the following Reaction Step B:

Reaction Step B

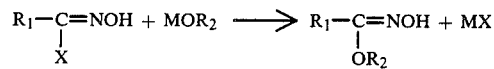

wherein $R_1$ and $R_2$ are as described above and M is an Alkali or Alkaline Earth metal. In step 2, the reaction of the Alkali metal or an Alkaline earth metal alcoholate and the 1-haloaldoxime is carried out in the organic solvent which is non-reactive with the haloaldoxime. In the preferred embodiments, this solvent is selected from the group of solvents which are permissible for use in the first step of the process of this invention. Generally, essentially stoichiometric quantities of the alkoxide salt are employed, although, it should be understood that the quantity of alkoxide salt employed can vary from stoichiometric to as much as a 100 percent excess. In the preferred embodiments of this reaction, the quantity of alkoxide salt employed will vary from stoichiometric to an excess of 50 percent. Usually where the 1-halo substituted oxime compound is produced and used in situ, sufficient alkoxide is added to neutralize HX and formed in the first step.

Useful alcoholate reactants include the alcoholate derivatives of aliphatic alkanols in which $R_2$ of the above formula is alkyl such as methyl, ethyl, propyl, hexyl, isopropyl, isobutyl, decyl, pentyl and the like; in which $R_2$ is alkenyl such as allyl, vinyl, 2-pentenyl, 3-butenyl, 4-hexenyl, and the like; and in which $R_2$ is alkynyl as for example 2-pentynyl, 3-hexynyl, 2-butynyl, 1-decynyl, 2-hexynyl, propynyl, 4-octynyl, and the like. Other useful alcoholate reactants are those derived from cycloaliphatic alkanols in which $R_2$ of the above formula is a cyclic group as for example a cycloalkyl group such as cycloheptyl, cyclohexyl, cyclopentyl and the like, or a cycloalkenyl group such as 2-cyclohexenyl, 3-cycloheptenyl, 2-cyclopentenyl and the like. Illustrative of still other useful alcoholate reactants are those derived from aromatic alcohols and phenols in which $R_2$ is an aromatic function such as phenyl, benzyl, naphthyl, phenethyl, benzothienyl, benzofuranyl, and the like. Of course as previously noted these $R_2$ functions may be substituted with one or more functional groups which are non-reactive under process conditions of the second essential step of the process of this invention. Such permissible functional groups include halogen, alkyl, alkoxy, cyano, nitro, carboxy, alkoxycarbonyl, amido, perhaloalkyl, and the like.

The alcoholates utilized as reactants in the process of this invention as well as methods for their preparation are well known in the art. For example, Alkaline earth metal and Alkali metal alcoholates can be readily prepared by reacting the elemental Alkaline earth metal or alkali metal, respectively, with the corresponding hydroxy compound. While any alkali metal or Alkaline earth metal alcoholate of the formula $R_2OM$ can be used in the process of this invention, sodium alkoxides are preferred for use. In the particularly preferred embodiments of this invention sodium alkoxide of the formula $R_2O^-Na^+$ in which $R_2$ is alkyl having from 1 to about 7 carbon atoms, phenylalkyl having from 7 to about 14 carbon atoms, alkenyl having from 2 to about 7 carbon atoms, cycloalkyl having from about 5 to about 10 carbon atoms and alkoxyalkyl having from 2 to about 8 carbon atoms are used. Amongst those alkoxide compounds for use in the particularly preferred embodiments of the invention, those alkoxide compounds in which $R_2$ is alkyl having from 1 to about 4 carbon atoms, alkenyl having from 2 to about 5 carbon atoms, and phenylalkyl having from 7 to about 11 carbon atoms are most preferred.

The temperature employed in the alcoholate addition step are usually in the same range as those employed in the halogenation step, i.e., the reaction is favored by temperatures of below room temperature because of the tendency of the 1-halo oxime compounds to decompose at higher temperatures. Temperatures within the range of from about $-5°$ C. to about 30° C. are preferred, and reaction temperatures of from about 0° C. to about 10° C. are particularly preferred.

The process of this invention is carried out over a period of time to produce the desired 1-organooxyaldoxime compound of the formula:

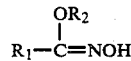

in adequate yield. In general, residence times can vary from about a few minutes to 24 hours or longer. In most instances, when employing preferred reaction conditions, reaction times will be found to vary from about 1 hour to about 3 hours. Reaction time is influenced to a significant degree by the reactants and their concentrations; the reaction temperature; the choice and concentration of reaction solvent; and by other factors known to those skilled in the art.

The process of this invention can be conducted in a batch, semicontinuous or continuous fashion. The reaction can be conducted in a single reaction zone or in a plurality of reaction zones, in series or in parallel or it may be conducted intermittently or continuously in an elongated tubular zone or series of such zones. The materials of construction employed should be inert to the reactants during the reaction and the fabrication of the equipment should be able to withstand the reaction temperatures and pressure.

The reaction zone can be fitted with one or more internal and/or external heat exchanger(s) in order to control undue temperature fluctuations, or to prevent any possible "runaway" reaction temperatures. In preferred embodiments of the process, agitation means to vary the degree of mixing of the reaction mixture can be employed. Mixing by vibration, shaking, stirring, rotation, oscillation, ultrasonic vibration or the like are all illustrative of the type of agitation means contemplated. Such means are available and well known to those skilled in the art.

The reactants and reagents may be initially introduced into the reaction zone batchwise or it may be continuously or intermittently introduced in such zone during the course of the process. Means to introduce and/or adjust the quantity of reactants introduced, either intermittently or continuously into the reaction zone during the course of the reaction can be conveniently utilized in the process especially to maintain the desired molar ratio of the reaction solvent, reactants and reagents.

The product 1-organo substituted oxime compound can be isolated from the reaction mixture and purified employing conventional techniques. Illustrative of such techniques are evaporated, distillation, solvent extraction and recrystallization.

The N-hydroxy organo imidate compounds prepared in accordance with the process of this invention have many and varied uses. For example, such compounds can be reacted with various carbamoyl halide compounds, such as N-methylcarbamoyl chloride, to form the corresponding carbamoyloxime (carbamate) compounds which have pesticidal activity. Such procedures are well known in the pesticidal and organic synthesis arts and will not be described herein in great detail.

The following specific examples are presented to more particularly illustrate the invention.

EXAMPLE I

Preparation of Ethyl N-Hydroxyacetimidate

A 3-neck, 250 mL flask was fitted with a gas bubbler, a drying tube and a thermometer. Acetaldehyde oxime (5.9 g; 0.1 mol) mixed with chloroform (100 mL) was placed in the flask and a PTFE-coated 1" magnetic stirring bar was introduced. The flask was placed in a cooling bath containing a mixture of ice and salt, which in turn was placed over a magnetic stirrer. Maintaining the temperature of the solution between 0° and $-5°$ C., chlorine gas was added slowly from a lecture bottle placed on a top-loading balance. Chlorine addition was continued until a stoichiometric amount with slight excess (7.2 g; 0.101 mol) of the gas was introduced (1 hour). The resulting solution was light blue in color, characteristic of chloroacetaldehyde oxime.

In the meantime, in another 3-neck, 500 mL flask fitted with a jacketed dropping funnel, thermometer and condenser with drying tube was prepared a solution of sodium ethoxide by dissolving freshly cut sodium (4.6 g; 0.20 mol) in absolute ethanol (125 mL). Stirring was provided in this flask using a magnetic stirring bar and the flask was cooled in ice bath. The bluish chloroacetaldehyde oxime solution was placed in the jacketed dropping funnel which was cooled using refrigerated coolant passed through the jacket (0° C.).

Chloroacetaldehyde oxime solution was slowly added to the sodium ethoxide solution (1 hour) with cooling and stirring. The resulting turbid solution was then heated at 60° C. for 4 hours and cooled. HCl gas was bubbled into liquid to bring the pH to 7 from 11.8. The white solid was filtered off and the clear filtrate evaporated under reduced pressure to remove the solvents. More turbidity developed and the liquid was filtered again. The clear and virtually colorless liquid (16.5 g) was analyzed by gas chromatography. The major component (56.6%) was identified as ethyl N-hydroxyacetimidate, by comparison with an authentic sample obtained from Aldrich. Methanol and chloroform constituted the other significant components. Yield was 90.5%.

EXAMPLE II

Preparation of Methyl N-Hydroxyacetimidate)

As in Example I, acetaldehyde oxime (5.9 g; 0.1 mol) in chloroform (100 mL) was chlorinated using chlorine gas introduced at 0° to −5° C. The bluish solution of chloroacetaldehyde oxime was placed in a 250 mL dopping funnel with jacket and circulating coolant for maintaining the contents cold.

The dropping funnel was attached to a 3-neck 500 mL flask fitted with a thermometer and condenser in the other openings. A solution of sodium methoxide in methanol (Aldrich, 25% by weight, 41 g; 0.19 mole) was placed in the flask and absolute methanol (50 mL) was added to it. To the clear solution the chloroform solution was slowly added with minimum cooling in a water bath (maximum 35° C.) and with stirring using a magnetic stirring bar. After completion of addition the solution was heated at 60° C. for 2½ hours. Terminal pH was 9.5. Hydrogen chloride gas was slowly added after cooling to 0° C. to bring pH to 7. The white precipitated of sodium chloride was filtered off and the filtrate concentrated under reduced pressure.

Gas chromatographic analysis of the concentrated solution (14.6 g) showed that it contained 48.8% of methyl N-hydroxyacetimidate. Identity of the product was confirmed by GC-mass spec analysis. Yield was 80.1%.

EXAMPLE III

Preparation of Methyl N-Hydroxyacetimidate

In a 250 ml flask, as in Example I, acetaldehyde oxime (5.9 g; 0.1 mol) mixed with absolute methanol (100 mL) was chlorinated in the cold (−5 to 0° C.) using chlorine gas delivered from a weighed lecture bottle. The clear bluish solution was placed in a cooled, jacketed dropping funnel which in turn was attached to a 500 mL 3-neck flask. This flask, fitted with a thermometer and condenser, was provided with magnetic stirring bar. Sodium methoxide solution (25 weight %; 50 g; 0.23 mol) in methanol was added to the flask and with stirring and minimal cooling the bluish solution was added slowly. On completion of addition, the thin white slurry was heated under reflux (66° C.) for 2½ hours. It was cooled to 0° C. and HCl gas was bubbled to bring pH to 7 from 11. The white slurry was filtered and sodium chloride removed, and the clear colorless solution was concentrated under reduced pressure and analyzed by gas chromatography to be a virtually pure solution of methyl-N-hydroxyacetimidate in methanol (19 g; 43.5%). Yield 92.8%.

EXAMPLE IV

Preparation of α-Phenoxy Propionaldehyde Oxime

Using the procedure of Example I, propionaldehyde oxime in carbon tetrachloride is brominated with bromine introduced at −5° to 0° C. To the resulting solution of 1-bromo-propionaldehyde oxime is added dropwise with stirring a suspension of sodium phenoxide in carbon tetrachloride. The reaction is allowed to go to completion and any residual sodium phenoxide is neutralized with hydrogen bromide gas. The precipitated sodium bromide is collected by filtration, and the filtrate concentrated under reduced pressure to provide the desired α-phenoxy propionaldehyde oxime.

EXAMPLE V

Preparation of 1-tert-Butoxy-2-phenylacetaldehyde Oxime

Using the procedure of Example I, phenyl acetaldehyde oxime in chloroform is reacted with chlorine gas introduced at −5° to 0° C. To the resulting solution of 1-chlorophenyl acetaldehyde oxime is added dropwise with stirring a solution of potassium t-butoxide in t-butanol. The reaction is allowed to go to completion and any residual potassium t-butoxide is neutralized with hydrogen chloride gas. The precipitated potassium chloride is removed by filtration, and the filtrate concentrated under reduced pressure to provide the desired 1-(t-butoxy)-2-phenyl acetaldehyde oxime.

EXAMPLE VI

Preparation of 1-Benzyloxy-3-chloro Pivalaldehyde Oxime

Using the procedure of Example I, 3-chloro pivaladehyde oxime in carbon tetrachloride is stirred with chlorine gas introduced at −5° to 0° C. To the resulting solution of 1,3-dichloropivalaldehyde oxime is added dropwise with stirring a solution of sodium benzyl alcoholate in benzyl alcohol. The reaction is allowed to go to completion and any residual alcoholate is neutralized with HCl gas. The precipitated sodium chloride is collected by filtration, and the filtrate concentrated under reduced pressure to provide the desired 1-benzyloxy-3-chloro pivaldehyde oxime.

EXAMPLE VII

Preparation of 1-methoxy-n-butyraldehyde oxime

Using the procedure of Example I, n-butyraldehyde oxime in methanol is treated with chlorine gas introduced at 0° to 5° C. To the resulting solution of 1-chloro-n-butyraldehyde oxime is added dropwise with stirring a solution of magnesium methylate in methanol. The reaction is allowed to go to completion and any residual magnesium methylate is neutralized with HCl gas. The precipitated magnesium chloride is removed by filtration, and the filtrate concentrated under reduced pressure to provide the desired 1-methoxy-n-butyraldehyde oxime.

What is claimed is:

1. A process for preparing a compound of the formula:

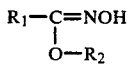

wherein:
R$_1$ is substituted or unsubstituted alkyl, alkoxyalkyl, cycloalkyl or phenylalkyl wherein permissible substituents are one or more halogen, nitro, cyano or perhaloalkyl groups; and
R$_2$, is alkyl, alkenyl, alkynyl, alkoxyalkyl, cycloalkyl, cycloalkenyl, phenyl or phenylalkyl either unsubstituted or substituted with one or more cyano, nitro, halogen, alkyl, alkoxy, alkylthio, arylthio, perhaloalkyl, alkylsulfinyl, alkylsulfonyl, amido, or alkoxycarbonyl groups, said process comprising the steps of:
(a) reacting an oxime compound of the formula R$_1$CH=NOH with a halogenating agent under substantially anhydrous conditions in an organic solvent which is substantially non-reactive with said halogenating agent under the reaction conditions to form the corresponding 1-halosubstituted oxime compound of the formula R$_1$C(X)=NOH wherein X is halogen; and
(b) reacting said 1-halosubstituted oxime compound in said solvent under substantially anhydrous conditions with an Alkali metal or Alkaline Earth metal alcoholate of the formula R$_2$OM wherein M is an Alkali metal or Alkaline Earth metal cation.

2. A process according to claim 1 wherein R$_1$ is alkyl having from 1 to about 7 carbon atoms and phenylalkyl having from 7 to about 14 carbon atoms.

3. A process according to claim 2 wherein R$_1$ is alkyl having from 1 to about 4 carbon atoms or phenylalkyl having from 7 to about 11 carbon atoms.

4. A process according to claim 3 wherein R$_1$ is alkyl having from 1 to about 4 carbon atoms.

5. A process according to claim 4 wherein R$_1$ is methyl, ethyl, propyl or isopropyl.

6. A process according to claim 1 wherein said 1-halosubstituted oxime compound is reacted with an alkali metal alcoholate.

7. A process according to claim 6 wherein said 1-halo substituted oxime compound is reacted with sodium alcoholate.

8. A process according to claim 1 wherein R$_2$ is selected from the group consisting of alkyl having from 1 to about 7 carbon atoms, alkenyl having from 2 to about 7 carbon atoms, phenylalkyl having from 7 about 14 carbon atoms, cycloalkyl having from about 5 to about 10 carbon atoms and alkoxyalkyl having from 2 to about 8 carbon atoms.

9. A process according to claim 8 wherein R$_2$ is alkyl having from 1 to about 4 carbon atoms, alkenyl having from 2 to about 5 carbon atoms, and phenylalkyl having from 7 to about 11 carbon atoms.

10. A process according to claim 9 wherein R$_2$ is alkyl having from 1 to about 4 carbon atoms.

11. A process according to claim 10 wherein R$_2$ is methyl, ethyl, propyl or isopropyl.

12. A process according to claim 9 wherein R$_2$ is alkenyl having from 2 to about 5 carbon atoms.

13. A process according to claim 12 wherein said R$_2$ is allylvinyl, 2-propenyl or 3-butenyl.

14. A process according to claim 9 wherein R$_2$ is phenylalkyl having from 7 to about 11 carbon atoms.

15. A process according to claim 14 wherein R$_2$ is benzyl or phenethyl.

16. A process according to claim 1 wherein said halogenation agent is an elemental halogen.

17. A process according to claim 16 wherein said halogen is chlorine.

18. A process according to claim 1 wherein said organic solvent is selected from the group consisting of alcohols and halo carbons.

19. A process according to claim 18 wherein said organic solvent is an alcohol.

20. A process according to claim 19 wherein said solvent is methanol.

21. A process according to claim 1 wherein step (a) is carried out at a temperature of less than about 25° C.

22. A process according to claim 21 wherein said temperature is from about 10° C. to about −10° C.

23. A process according to claim 1 wherein:
R$_1$ is methyl; and
R$_2$ is methyl or ethyl.

24. A process for preparing a compound of the formula:

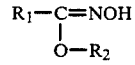

wherein:
R$_1$ is alkyl having from 1 to about 7 carbon atoms and phenylalkyl having from 7 to about 14 carbon atoms; and
R$_2$ is alkyl having from 1 to about 7 carbon atoms, alkenyl having from 2 to about 7 carbon atoms, phenylalkyl having from 7 to about 14 carbon atoms, cycloalkyl having from about 5 to about 10 carbon atoms and alkoxyalkyl having from 2 to about 8 carbon atoms, said process comprising the steps of:
(a) reacting an oxime compound of the formula R$_1$CH=NOH with a halogenating agent under substantially anhydrous conditions in an organic solvent which is substantially non-reactive with said halogenating agent under the reaction conditions to form the corresponding 1-halosubstituted oxime compound of the formula R$_1$C(X)=NOH wherein X is halogen; and
(b) reacting said 1-halosubstituted oxime compound in said solvent under substantially anhydrous conditions with an Alkali metal or Alkaline Earth metal alcoholate of the formula R$_2$OM wherein M is an Alkali metal or Alkaline Earth metal cation.

* * * * *